US010203303B2

(12) United States Patent
Astley et al.

(10) Patent No.: US 10,203,303 B2
(45) Date of Patent: Feb. 12, 2019

(54) APPARATUS AND ASSOCIATED METHODS FOR ANALYTE DETECTION

(71) Applicant: Nokia Technologies Oy, Espoo (FI)

(72) Inventors: Michael Astley, Cambridge (GB); Di Wei, Cambridge (GB); Stefano Borini, Cambridge (GB); Jani Kivioja, Cambourne (GB)

(73) Assignee: NOKIA TECHNOLOGIES OY, Espoo (FI)

( * ) Notice: Subject to any disclaimer, the term of this patent is extended or adjusted under 35 U.S.C. 154(b) by 264 days.

(21) Appl. No.: 15/021,744

(22) PCT Filed: Sep. 18, 2014

(86) PCT No.: PCT/FI2014/050713
§ 371 (c)(1),
(2) Date: Mar. 14, 2016

(87) PCT Pub. No.: WO2015/052370
PCT Pub. Date: Apr. 16, 2015

(65) Prior Publication Data
US 2016/0223490 A1 Aug. 4, 2016

(30) Foreign Application Priority Data
Oct. 9, 2013 (GB) .................................. 1317878.5

(51) Int. Cl.
*G01N 27/404* (2006.01)
*G01N 27/416* (2006.01)
(Continued)

(52) U.S. Cl.
CPC ....... *G01N 27/4166* (2013.01); *G01N 27/307* (2013.01); *G01N 27/308* (2013.01);
(Continued)

(58) Field of Classification Search
CPC ......... G01N 27/327–27/3272; G01N 27/3275; G01N 27/3276; G01N 27/333; G01N 27/403; G01N 27/27; G01N 33/4836
See application file for complete search history.

(56) References Cited

U.S. PATENT DOCUMENTS 4,143,177 A * 3/1979 Kovac .................... G01K 13/00
324/687
4,280,115 A * 7/1981 Farrington ........... G01N 27/048
29/610.1
(Continued)

FOREIGN PATENT DOCUMENTS

CN 101126734 A 2/2008
CN 101275923 A 10/2008
(Continued)

OTHER PUBLICATIONS

English langauge translation of the First Office Action from State Intellectual Property Office of People's Republic of China for application No. 201480055338.5, Office action dated Oct. 10, 2017 (Year: 2017).*
(Continued)

*Primary Examiner* — Alexander S Noguerola
(74) *Attorney, Agent, or Firm* — Alston & Bird LLP (57) ABSTRACT

An apparatus comprising a plurality of first elongate electrodes (101) separated from a plurality of second transversely oriented elongate electrodes (102) by an electrolyte (103), the plurality of transversely oriented first (101) and second (102) electrodes forming an array of respective electrochemical sensor nodes at the spaced crossings thereof, wherein the first electrodes (101) are configured such that the interaction of an analyte with the first electrode (101) at a sensor node affects an electrical property of the sensor node, and wherein the apparatus comprises respective terminals connected to each electrode (101, 102) for elec-
(Continued)

trical connection to a measurement circuit to enable determination of the presence and/or amount of analyte at a particular sensor node based on a measurement of the electrical property of that sensor node.

19 Claims, 7 Drawing Sheets

(51) Int. Cl.
    *G01N 27/407*     (2006.01)
    *G01N 27/30*     (2006.01)
    *G01N 33/483*     (2006.01)

(52) U.S. Cl.
    CPC ..... *G01N 27/4071* (2013.01); *G01N 27/4074* (2013.01); *G01N 27/4075* (2013.01); *G01N 33/4836* (2013.01)

(56) References Cited

U.S. PATENT DOCUMENTS

| | | | | |
|---|---|---|---|---|
| 5,212,050 | A * | 5/1993 | Mier | B01L 3/0268 422/930 |
| 6,764,648 | B1 * | 7/2004 | Roach | G01N 27/44704 204/451 |
| 7,074,519 | B2 | 7/2006 | Kuhr et al. | |
| 8,357,559 | B2 | 1/2013 | Segal et al. | |
| 8,381,575 | B2 * | 2/2013 | Seo | G01N 27/223 73/29.02 |
| 2002/0039743 | A1 * | 4/2002 | Hashimoto | C12Q 1/6825 435/6.11 |
| 2003/0141188 | A1 | 7/2003 | Imamura et al. | |
| 2004/0099531 | A1 * | 5/2004 | Srinivasan | G01N 33/5438 204/412 |
| 2004/0132220 | A1 | 7/2004 | Fish | |
| 2004/0146863 | A1 * | 7/2004 | Pisharody | C12Q 1/003 435/6.11 |
| 2007/0227911 | A1 | 10/2007 | Wang et al. | |
| 2007/0252713 | A1 | 11/2007 | Rondoni et al. | |
| 2010/0079130 | A1 | 4/2010 | Hong et al. | |
| 2011/0052813 | A1 * | 3/2011 | Ho | B82Y 30/00 427/256 |
| 2011/0244585 | A1 | 10/2011 | Mayne-L'Hermite et al. | |
| 2012/0183856 | A1 | 7/2012 | Cui et al. | |
| 2012/0321785 | A1 | 12/2012 | Rogers et al. | |
| 2013/0033310 | A1 | 2/2013 | Liu | |
| 2013/0316340 | A1 * | 11/2013 | Kelley | C12Q 1/6825 435/6.11 |

FOREIGN PATENT DOCUMENTS

| | | |
|---|---|---|
| CN | 101960299 A | 1/2011 |
| CN | 102980933 A | 3/2013 |
| EP | 1211633 | 6/2002 |
| GB | 2516932 A | 2/2015 |
| JP | H08193854 | 7/1996 |
| WO | 9322678 | 11/1993 |
| WO | 03027658 | 4/2003 |
| WO | 2008/130149 A1 | 10/2008 |
| WO | 2015/007948 A | 1/2015 |

OTHER PUBLICATIONS

English langauge translation of the Second Office Action from State Intellectual Property Office of People's Republic of China for application No. 201480055338.5, Office action dated May 29, 2018 (Year: 2018).*
Yao et al., "The effect of ambient humidity on the electrical properties of graphene oxide films", Nanoscale Research Letters, Dec. 2012, pp. 1-7.
Prezioso et al., "Graphene oxide as a practical solution to high sensitivity gas sensing", J. Phys. Chem, 2013, 117, pp. 10683-10690.
Li et al., "Sensors and Actuators B: Chemical", Science Direct, vol. 123, No. 2, 2007, pp. 651-660.
"Seacoast Sciences technology", Seacoast Science, Retrieved on Apr. 17, 2017, Webpage available at : http://www.seacoastscience.com/technology.htm.
Takashi et al., "Optical and Electric Multifunctional CMOS Image Sensors for On-Chip Biosensing Applications", Materials, vol. 4, No. 1, 2011, pp. 84-102.
Li et al., "Influence of water on the electronic structure of metal-supported graphene: Insights from van der Waals density functional theory", Physical Review B, vol. 85, No. 8, 2012, pp. 1-10.
Dai et al., "Sensors and Sensor Arrays Based on Conjugated Polymers and Carbon Nanotubes", The Scientific Journal of IUPAC, vol. 74, No. 9, Jan. 2002, pp. 1753-1772.
Qi et al., "Toward Large Arrays of Multiplex Functionalized Carbon Nanotube Sensors for Highly Sensitive and Selective Molecular Detection", Nano Letters, vol. 3, No. 3, 2003, pp. 347-351.
Yang et al., "Memristive Devices for Computing", Nature Nanotechnology, vol. 8, 2013, pp. 13-24.
Extended European Search Report received for corresponding European Patent Application No. 14851651.1, dated Apr. 10, 2017, 7 pages.
Office action received for corresponding GB Patent Application No. 1317878.5, dated Apr. 21, 2017, 6 pages.
Office action received for corresponding GB Patent Application No. 1317878.5, dated Dec. 6, 2017, 3 pages.
International Search Report and Written Opinion received for corresponding Patent Cooperation Treaty Application No. PCT/FI2014/050713 , dated Dec. 12, 2014, 11 pages.
Search Report received for corresponding GB Patent Application No. 1317878.5, dated Feb. 28, 2014, 3 pages.
Office action received for corresponding Chinese Patent Application No. 201480055338.5, dated Oct. 10, 2017, 9 pages of office action and no page of translation available.
Office action received for corresponding GB Patent Application No. 1317878.5, dated Aug. 15, 2017, 3 pages.
Office action received for corresponding Chinese Patent Application No. 201480055338.5, dated May 29, 2018, 3 pages of office action and no page of translation available.
Office Action for European Application No. 14 851 651.1 dated Nov. 9, 2018, 7 pages.

* cited by examiner

Figure 12

APPARATUS AND ASSOCIATED METHODS FOR ANALYTE DETECTION

RELATED APPLICATION

This application was originally filed as PCT Application No. PCT/FI2014/050713 filed Sep. 18, 2014 which claims priority benefit from GB Patent Application No. 1317878.5, filed Oct. 9, 2013.

TECHNICAL FIELD

The present disclosure relates to the field of sensors, associated methods and apparatus, and in particular concerns an apparatus comprising an array of electrochemical sensor nodes for use in determining the presence and/or amount of an analyte at a particular sensor node based on a measurement of an electrical property of that sensor node. Certain disclosed example aspects/embodiments relate to portable electronic devices, in particular, so-called hand-portable electronic devices which may be hand-held in use (although they may be placed in a cradle in use). Such hand-portable electronic devices include so-called Personal Digital Assistants (PDAs) and tablet PCs.

The portable electronic devices/apparatus according to one or more disclosed example aspects/embodiments may provide one or more audio/text/video communication functions (e.g. tele-communication, video-communication, and/or text transmission, Short Message Service (SMS)/Multimedia Message Service (MMS)/emailing functions, interactive/non-interactive viewing functions (e.g. web-browsing, navigation, TV/program viewing functions), music recording/playing functions (e.g. MP3 or other format and/or (FM/AM) radio broadcast recording/playing), downloading/sending of data functions, image capture function (e.g. using a (e.g. in-built) digital camera), and gaming functions.

BACKGROUND

New and interesting sensor applications may be achieved by integrating large numbers of sensors into a device.

One or more aspects/embodiments of the present disclosure may or may not address this issue.

The listing or discussion of a prior-published document or any background in this specification should not necessarily be taken as an acknowledgement that the document or background is part of the state of the art or is common general knowledge.

SUMMARY

According to a first aspect, there is provided an apparatus comprising a plurality of first elongate electrodes separated from a plurality of second transversely oriented elongate electrodes by an electrolyte, the plurality of transversely oriented first and second electrodes forming an array of respective electrochemical sensor nodes at the spaced crossings thereof,
wherein the first electrodes are configured such that the interaction of an analyte with the first electrode at a sensor node affects an electrical property of the sensor node, and
wherein the apparatus comprises respective terminals connected to each electrode for electrical connection to a measurement circuit to enable determination of the presence and/or amount of analyte at a particular sensor node based on a measurement of the electrical property of that sensor node.

The first and second electrodes may be configured to exhibit a potential difference therebetween, or a change in potential difference therebetween, on interaction of the first electrode with the analyte. The first electrodes may be configured such that one or more of their electrochemical potential and electrical conductance are dependent upon the amount of analyte present.

The measurement circuit may form part of the apparatus.

The measurement circuit may be configured to measure the potential difference at the sensor nodes to enable determination of the presence and/or amount of analyte.

The apparatus may be configured such that the first and second electrodes at a sensor node serve as the anode and cathode of an electrochemical sensor. The apparatus may be configured such that the first and second electrodes at a sensor node serve as the anode and cathode of an electrochemical sensor, respectively. The second electrode may serve as a reference electrode with respect to which the potential of the first electrode is measured.

The apparatus may comprise a further electrode separated from the plurality of second electrodes by an electrolyte. The apparatus may be configured such that the first and further electrode at a sensor node serve as the anode and cathode of an electrochemical sensor. The apparatus may be configured such that the first and further electrode at a sensor node serve as the anode and cathode of an electrochemical sensor, respectively. The second electrode may serve as a reference electrode with respect to which the potential of the first electrode is measured. The second electrode may comprise ferrocene and the further electrode may comprise lithium.

The apparatus may comprise a feedback loop between the second electrode and the further electrode to hold the second electrode at a reference potential.

The measurement circuit may comprise one or more of a voltmeter, an analogue-to-digital converter and a schmitt trigger to enable determination of the presence and/or amount of analyte.

The measurement circuit may be configured to apply a varying potential difference between the first and second electrode at a sensor node and measure current peaks at the first electrode in response to the applied potential difference. The first electrode may be configured such that the position and/or size of the current peaks are dependent upon the presence and/or amount of analyte.

The measurement circuit may comprise one or more of a potentiostat and controller to enable determination of the presence and/or amount of analyte.

The plurality of first electrodes may be configured such that the electrical property of each sensor node is dependent upon the presence and/or amount of the same analyte. The first electrode at each sensor node may comprise the same material.

At least some of the plurality of first electrodes may be configured such that the electrical property of the respective sensor nodes is dependent upon the presence and/or amount of different analytes. The first electrodes at the respective sensor nodes may comprise different materials or the same material with different functionalizations to allow the presence and/or amount of the different respective analytes to be determined.

The measurement circuit may comprise a first multiplexer connected to the terminals of the plurality of first electrodes and a second multiplexer connected to the terminals of the plurality of second electrodes. The first and second multiplexers may be configured to enable the electrical property of a particular sensor node to be selectively determined.

The apparatus may be configured such that the plurality of first electrodes are arranged substantially parallel to one another, the plurality of second electrodes are arranged substantially parallel to one another, and the plurality of first electrodes are arranged substantially perpendicular to the plurality of second electrodes. The plurality of first electrodes and the plurality of second electrodes may be straight elongate electrodes or curvilinear elongate electrodes.

The apparatus may comprise microfluidic channels and associated pumps configured to deliver fluid to the sensor nodes for determination of the presence and/or amount of analyte within the fluid.

One or more of the first electrodes may comprise a graphene oxide film. The one or more first electrodes may comprise a metal mesh or layer of patterned metal on top of the graphene oxide film. One or more of the first electrodes may comprise graphene oxide and a conducting polymer in the form of a composite material. One or more of the second electrodes may comprise lithium oxide and/or manganese dioxide. The electrolyte may comprise one or more of polyvinylidene fluoride, polyacrylic, polyester and a polyethylene oxide derivative.

The analyte may comprise one or more of a chemical and biological species. The analyte may comprise one or more of a gas, liquid and vapour. The analyte may comprise water.

The apparatus may be one or more of an electronic device, a portable electronic device, a portable telecommunications device, a sensor array, and a module for any of the aforementioned devices.

According to a further aspect, there is provided a method comprising determining the presence and/or amount of analyte using an apparatus and a measurement circuit, the apparatus comprising a plurality of first elongate electrodes separated from a plurality of second transversely oriented elongate electrodes by an electrolyte, the plurality of transversely oriented first and second electrodes forming an array of respective electrochemical sensor nodes at the spaced crossings thereof, wherein the first electrodes are configured such that the interaction of an analyte with the first electrode at a sensor node affects an electrical property of the sensor node, and wherein the apparatus comprises respective terminals connected to each electrode for electrical connection to a measurement circuit to enable determination of the presence and/or amount of analyte at a particular sensor node based on a measurement of the electrical property of that sensor node.

According to a further aspect, there is provided a method of making an apparatus for use in determining the presence and/or amount of analyte, the method comprising:

providing an electrolyte in a spacing between a plurality of first elongate electrodes and a plurality of second transversely oriented elongate electrodes to form an array of respective electrochemical sensor nodes at the spaced crossings of the first and second electrodes, wherein the first electrodes are configured such that the interaction of an analyte with the first electrode at a sensor node affects an electrical property of the sensor node; and providing respective terminals connected to each electrode for electrical connection to a measurement circuit to enable determination of the presence and/or amount of analyte at a particular sensor node based on a measurement of the electrical property of that sensor node.

The steps of any method disclosed herein do not have to be performed in the exact order disclosed, unless explicitly stated or understood by the skilled person.

Corresponding computer programs (which may or may not be recorded on a carrier) for implementing one or more of the methods disclosed herein are also within the present disclosure and encompassed by one or more of the described example embodiments.

The present disclosure includes one or more corresponding aspects, example embodiments or features in isolation or in various combinations whether or not specifically stated (including claimed) in that combination or in isolation. Corresponding means for performing one or more of the discussed functions are also within the present disclosure.

The above summary is intended to be merely exemplary and non-limiting.

BRIEF DESCRIPTION OF THE FIGURES

A description is now given, by way of example only, with reference to the accompanying drawings, in which:—

DESCRIPTION OF SPECIFIC ASPECTS/EMBODIMENTS

The integration of large numbers of sensors into a device is not easy. For example, some existing sensor arrays require complex routing (for individually addressed nodes), the inclusion of active components in an array (for actively addressed arrays), or complex readout techniques (such as charge-transfer readout needed to measure mutual capacitance arrays). Thus, it is demanding to measure a large number of sensor sites independently.

There are existing chemical sensor arrays that involve each of the sensor sites being addressed individually by their own respective electrode terminals. This arrangement limits the size of the array to a relatively small number of sensor sites due to size limitations. In addition, electrochemical cell arrays have been proposed as sensor arrays and molecular electromechanical memory devices. In these structures, the cell voltage is modified by the oxidation state of molecules in the electrolyte material. Such a system needs complex geometries, such as microvials, to be manufactured into the structure. In addition, the sensors of the array are only sensitive to molecules in the liquids that form the electrolyte. There will now be described an apparatus and associated methods that may or may not provide a solution to one or more of these issues.

Figure 1:
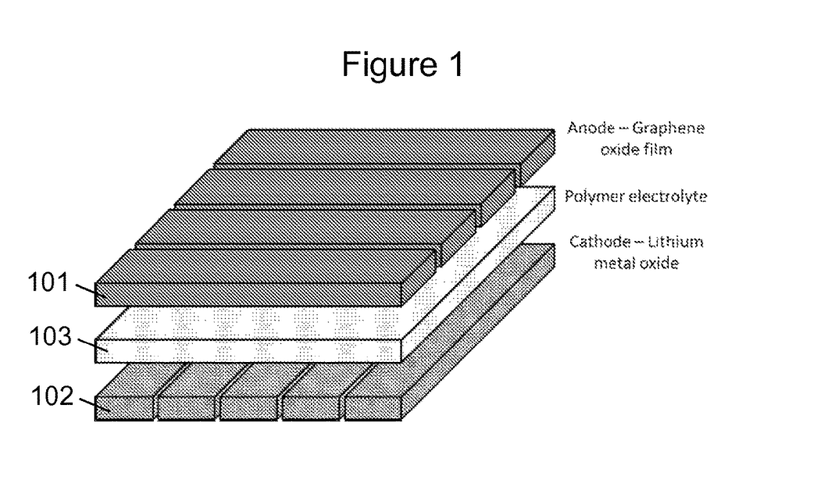
FIG. 1 shows an apparatus according to one embodiment of the present disclosure.

One embodiment of the present apparatus is illustrated in FIG. 1. The apparatus comprises a plurality of first (straight) elongate electrodes 101 separated from a plurality of second transversely oriented (straight) elongate electrodes 102 by an electrolyte 103 to form an array of respective electrochemical sensor nodes at the spaced crossings of the first 101 and second 102 electrodes. The first electrodes 101 are configured such that the interaction of an analyte with the first electrode 101 at a sensor node affects an electrical property of the sensor node. In this way, by connecting respective terminals to each electrode 101, 102, it is possible to determine the presence and/or amount of analyte at a particular sensor node based on a measurement of the electrical property of that sensor node.

An advantage of the present apparatus is its simplicity, which is a direct result of the electrochemical cell architecture. The spaced crossbar arrangement requires no sophisticated fabrication and can therefore be manufactured cheaply on a large scale using conventional techniques such as screen printing. In addition, relatively basic measurement electronics can be used for the electrical read-out, and since the analyte-sensitive components (i.e. the first electrodes 101) are located on the exterior of the apparatus, the sensor nodes can be used to detect analytes in the surrounding environment.

In this example, the plurality of first electrodes 101 are arranged substantially parallel to one another, the plurality of second electrodes 102 are arranged substantially parallel to one another, and the plurality of first electrodes 101 are arranged substantially perpendicular to the plurality of second electrodes 102. Nevertheless, the electrodes 101, 102 could be arranged in other ways provided that they form a plurality of spaced crossings.

The apparatus may be used to detect atmospheric analyte species if the first electrodes 101 are exposed to the external environment, or it may be used to detect analytes contained within sample fluids. In the latter scenatio, the apparatus may comprise microfluidic channels and associated pumps (not shown) configured to deliver fluid to the sensor nodes for determination of the presence and/or amount of analyte within the fluid.

Figure 2:
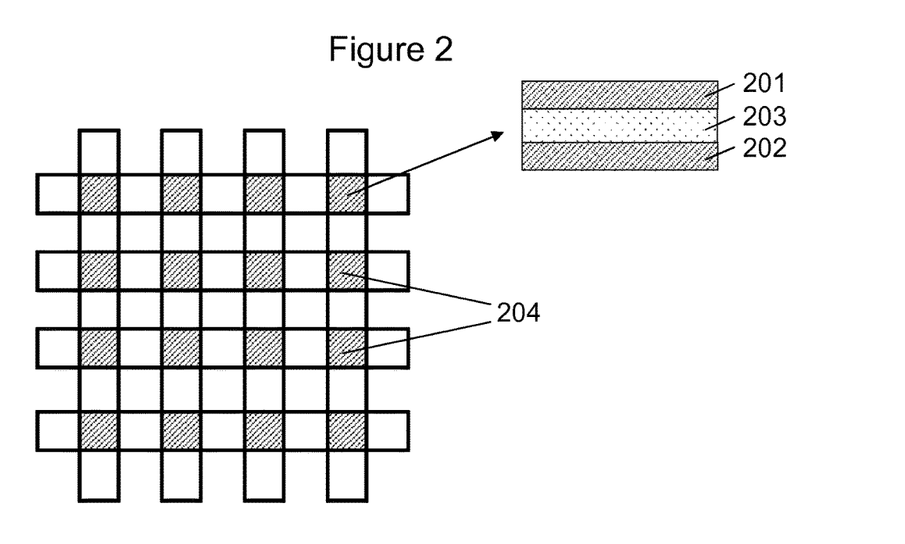
FIG. 2 shows greater detail of the sensor nodes of the apparatus of FIG. 1.

FIG. 2 is a plan view of the apparatus in FIG. 1 showing the sensor nodes 204 at the spaced crossings of the first 201 and second 202 electrodes. Each node 204 is effectively a separate electrochemical cell comprising a cathode (either the first 201 or second 202 electrode), an anode (the remaining electrode 202, 201) and an electrolyte 203. In some embodiments, the plurality of first electrodes 201 may be configured such that the electrical property of each sensor node 204 is dependent upon the presence and/or amount of the same analyte, which may be achieved in practice by forming the plurality of first electrodes 201 from the same material. In this scenario, the sensor array may be used to determine the location of the analyte based on the particular node 204 at which the analyte was detected, as well as determining its presence and/or quantity. This could be used, for example, in a breath-controlled user interface in which the electrochemical sensor nodes 204 are configured as humidity sensors to detect changes in the water content of the local environment.

In other embodiments, at least some of the plurality of first electrodes 201 (perhaps all of the first electrodes 201) may be configured such that the electrical property of the respective sensor nodes 204 is dependent upon the presence and/or amount of different analytes. This may be achieved by forming the first electrodes 201 from different materials, or by forming them from the same material with different functionalizations (i.e. with different chemical groups attached thereto), and could be used to create an electronic nose for detecting a number of different analyte species. As discussed later, graphene oxide is a promising platform for a wide variety of functionalizations, so a large number of different sensors could be made based on this technique.

Figure 3:
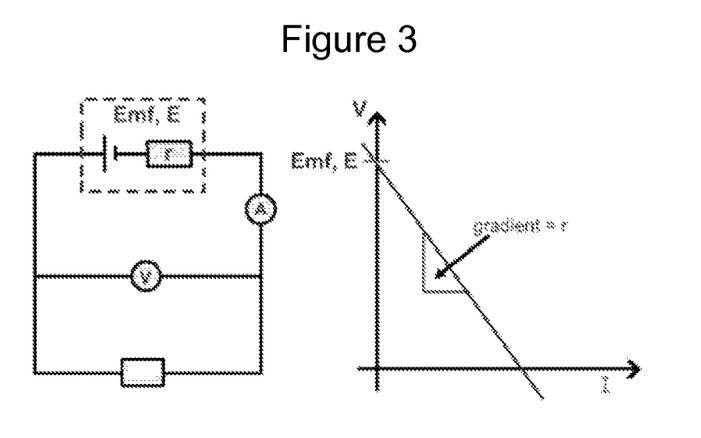
FIG. 3 shows a conventional battery and associated I/V curve.

A battery may be modelled as an electromotive force in series with an internal resistance, as shown in FIG. 3. The potential difference (V) of a battery is related to its electromotive force (E) and internal resistance (r) by $$V = E - Ir \qquad \text{Equation 1}$$

where I is the current flowing round the circuit as a result of the potential difference. In one embodiment of the present apparatus, the first and second electrodes at a sensor node are configured to exhibit a potential difference (V) therebetween on interaction of the first electrode with the analyte, the first electrode configured such that one or more of its electrochemical potential and electrical conductance are dependent upon the amount of analyte present. Since the electrical conductance and electrochemical potential of the first electrode influence the internal resistance (r) and electromotive force (E) of the sensor node, respectively, the presence of the analyte strongly affects the potential difference (V) between the first and second electrodes. In this way, the presence and/or amount of analyte can be determined based on the potential difference (V) of the sensor node. Furthermore, since the analyte creates the potential difference between the first and second electrodes, which in turn is used to sense the analyte, this embodiment of the present apparatus may be viewed as a self-powered sensor array (or at least a module thereof). To enable this approach to work, the first electrode should comprise a material whose electrical conductance and/or electrochemical potential vary with the amount of analyte present. The type of electrode material used, however, will depend on the specific analyte (i.e. the particular chemical or biological species) being detected and the environment in which the apparatus is used.

Figure 4:
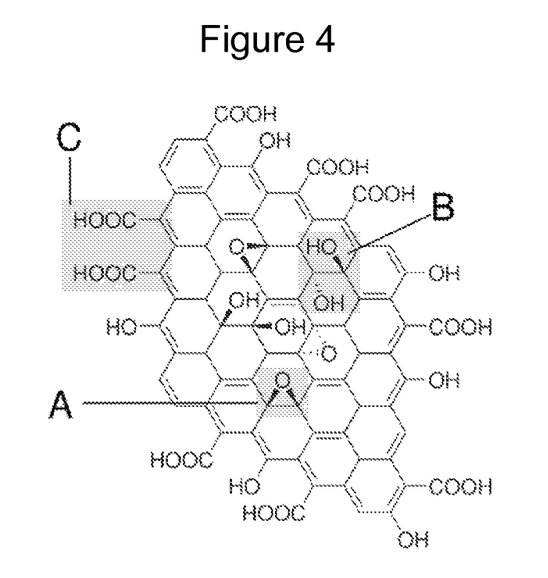
FIG. 4 shows the chemical structure of graphene oxide.

One example is graphene oxide for detecting water (in gaseous, liquid and/or vapour form) in the air, i.e. as a humidity sensor. Graphene oxide may be considered as graphene with one or more functional groups attached thereto, such as carboxyl (C), hydroxyl (B) and/or epoxy (A) groups as shown in FIG. 4. A battery which uses a thin graphene oxide film as the anode has an internal resistance (r) approximated by $$r = r_0 \exp(-H/H_0) \qquad \text{Equation 2}$$

where H is the relative humidity and $r_0$ and $H_0$ are constants which are dependent upon the anode's particular structure and geometry. The anode's conductance can be tailored to a specific application by varying the geometry of the electrode and incorporating other materials. For example, by depositing a metal mesh on top of the graphene oxide film, the internal resistance of the battery may be decreased by orders of magnitude due to the mesh bridging across discontinuities in the graphene oxide film. Alternatively, a layer of patterned metal may be deposited on top of the graphene oxide film, the resistance of which can be engineered by tailoring the metal pattern. Furthermore, if the conductivity of the electrode is intrinsically low, it may be increased using a conductive polymer (e.g. polyaniline) to form a graphene oxide polymer composite.

The electromotive force of a battery depends on the relative alignment of the Fermi energy between the anode and cathode. It has been shown that water has an influence on the electronic structure of metal-supported graphene with a shift in Fermi level (electrochemical potential) on the order of 100 meV. Such a shift becomes more severe when graphene includes one or more carboxyl, hydroxyl and/or epoxy groups. The electrochemical potential of graphene oxide therefore varies greatly with changes in water concentration. This can be seen in FIG. 5, which shows open-circuit voltage measurements for a graphene oxide-based battery at different humidity levels. In this example, the battery had a graphene oxide-coated anode, a polyester electrolyte and a $LiCoO_2$ cathode. Other suitable materials for the cathode include lithium oxide and/or manganese diode, whilst the electrolyte may comprise one or more of polyvinylidene fluoride, polyacrylic, polyester and a polyethylene oxide derivative.

Figure 5:
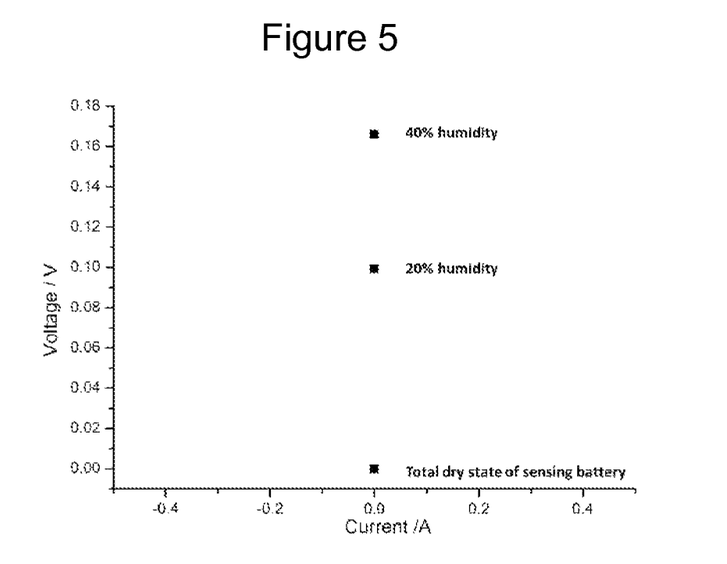
FIG. 5 shows open-circuit potential difference measurements for a graphene oxide-based battery at different humidity levels.

The change in output voltage (potential difference) of a graphene oxide-based battery with humidity is therefore caused not only by a change in the conductance of the graphene oxide, but also by a change in the electrochemical potential of the graphene oxide. The dependence of the electrochemical potential on the presence and/or amount of analyte can also provide information on the underlying chemical processes occurring across the sensor array. For example, it is possible to track the progress of a reaction as the reactant chemicals at difference locations on the sensor array mix through lateral diffusion.

The first electrode material and analyte are not limited solely to graphene oxide and water, respectively. Other examples include 2D transition metal dichalcogenides (e.g. $MoS_2$) for sensing triethylamine; graphene for sensing ammonia and $NO_2$; functionalised graphene (e.g. graphene functionalised with enzymes) for sensing glucose; silver nanoparticles for sensing ammonia; and porous silicone for sensing ammonia.

Figure 6:
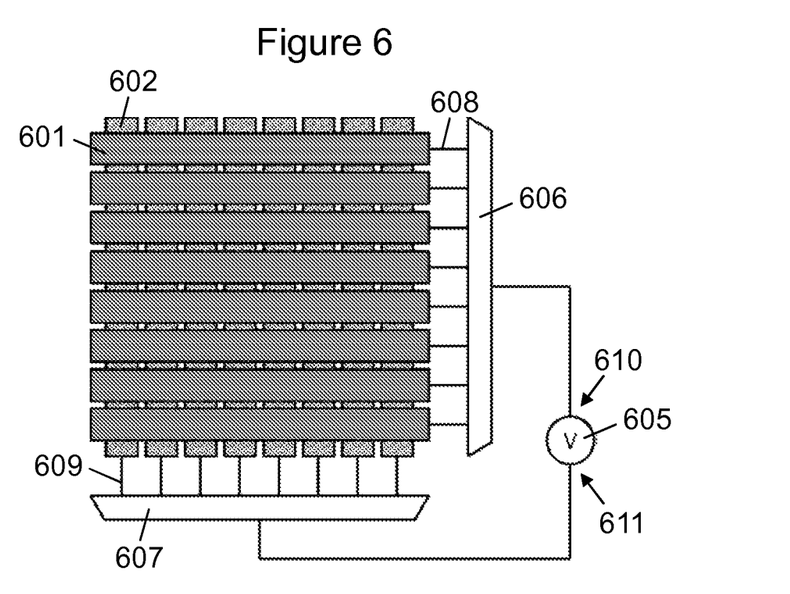
FIG. 6 shows the apparatus of FIG. 1 connected to a measurement circuit.

As mentioned above, the use of a spaced crossbar structure allows basic electronics to be used for detecting the state of each sensor node. FIG. 6 shows one example of a measurement circuit electrically connected to the apparatus of FIGS. 1 and 2 comprising a voltmeter 605 and first 606 and second 607 multiplexers. Additionally or alternatively, the measurement circuit may comprise an analogue-to-digital converter and a Schmitt trigger to enable threshold (i.e. qualitative) detection rather than a quantitative voltage measurement. This measurement circuit is configured to measure the potential difference at the sensor nodes to enable determination of the presence and/or amount of analyte. The first multiplexer 606 is connected to the terminals 608 of the plurality of first electrodes 601 and the second multiplexer 607 is connected to the terminals 609 of the plurality of second electrodes 602. The multiplexers 606, 607 are configured to enable the potential difference of a particular sensor node to be selectively determined by connecting one of the first electrode terminals 608 and one of the second electrode terminals 609 to respective terminals 610, 611 of the voltmeter 605.

In the embodiments described above, the apparatus is configured such that the first 601 and second 602 electrodes at a sensor node serve as the anode and cathode (either way round) of an electrochemical sensor, and the second electrode 602 serves as a reference electrode with respect to which the potential of the first electrode 601 is measured. With this configuration, therefore, the second electrode 602 acts both as a voltage reference and as a current source or drain.

Figure 7:
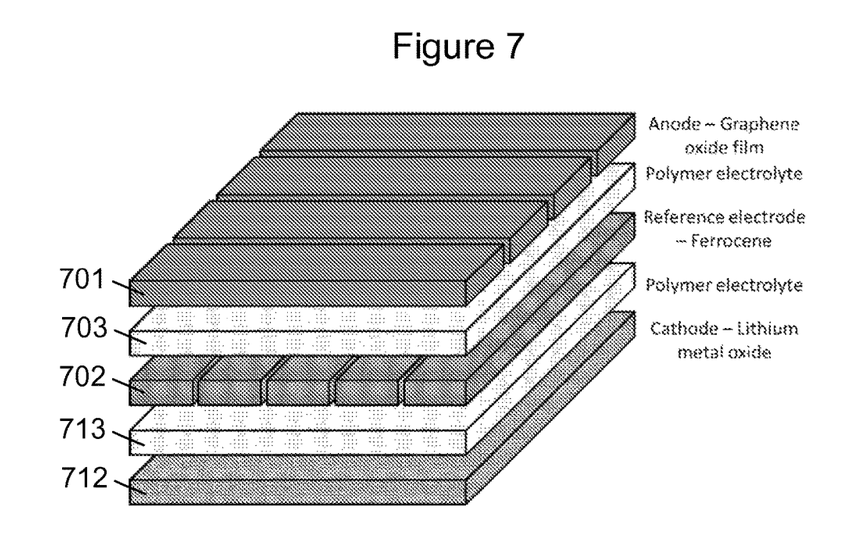
FIG. 7 shows an apparatus according to another embodiment of the present disclosure.

To improve the accuracy of the voltage measurements, the apparatus may comprise a further electrode 712 separated from the plurality of second electrodes 702 by an electrolyte 713 (which may be the same as the electrolyte 703 which separates the plurality of first electrodes 701 from the plurality of second electrodes 702), as shown in FIG. 7. The plurality of second electrodes 702 may be formed from ferrocene and the further electrode 712 may be formed from lithium. In this embodiment, the apparatus is configured such that the first 701 and further 712 electrode at a sensor node serve as the anode and cathode (either way round), and the second electrode 702 serves as the reference electrode. In this way, the potential of the first electrode 701 is measured with respect to the second electrode 702 (which is not involved in the electrochemical reactions) whilst the further electrode 712 acts as a current source or drain.

Figure 8:
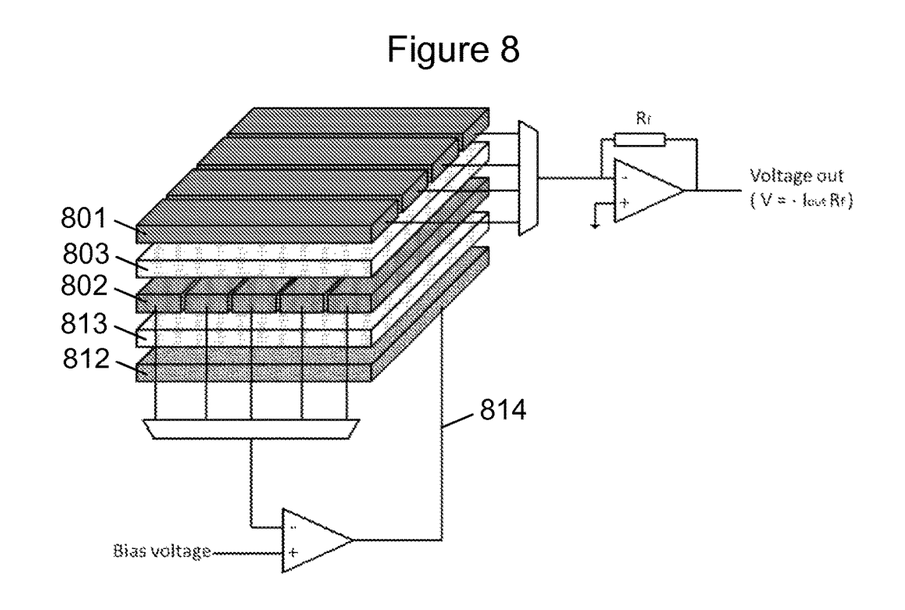
FIG. 8 shows the apparatus of FIG. 7 connected to a measurement circuit.

FIG. 8 shows a measurement circuit which is suitable for use with the embodiment of FIG. 7. In addition to the voltmeter and multiplexers (and/or analogue-to-digital converter and Schmitt trigger) of the previous measurement circuit, this measurement circuit further comprises a feedback loop 814 between the second electrode 802 and the further electrode 812 at a sensor node to hold the second electrode 802 at a reference potential and maintain a current between the first 801 and further 812 electrode.

Rather than using measurements of the potential difference to determine the presence and/or amount of analyte, the present apparatus may be configured for voltammetry by replacing the voltmeter of the measurement circuit with a potentiostat and controller (not shown). In this scenario, the potentiostat (under the influence of the controller) is configured to apply a varying potential difference between the first and second electrode at a sensor node and measure current peaks at the first electrode in response to the applied potential difference. To enable analyte detection/measurement, the first electrode is configured such that the position and/or size of the current peaks are dependent upon the presence and/or amount of analyte. This may be achieved by using an appropriate analyte-sensitive material at the first electrode, such as graphene oxide for detecting water.

Figure 9A:
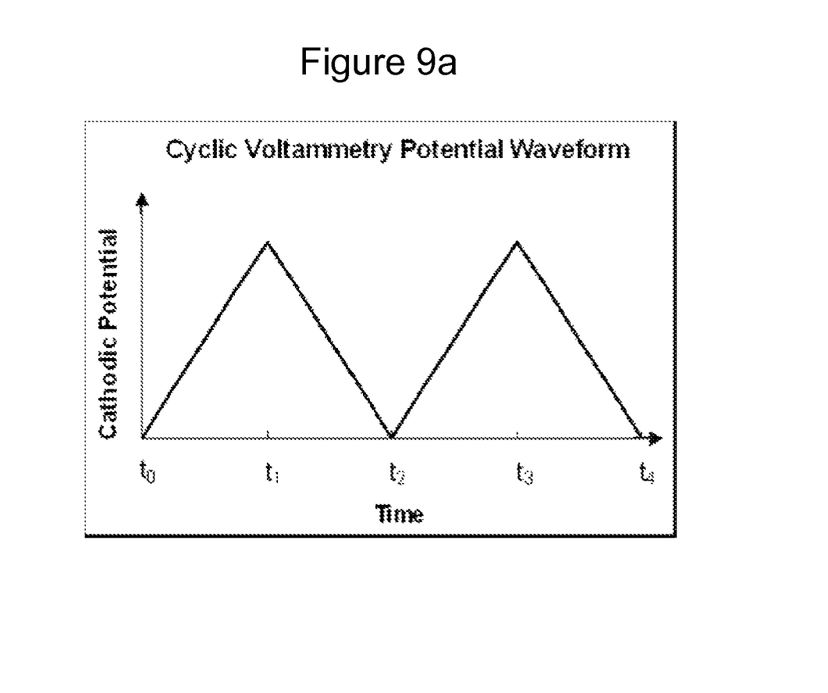
FIG. 9a shows a typical potential waveform for cyclic voltammetry measurements.
Figure 9B:
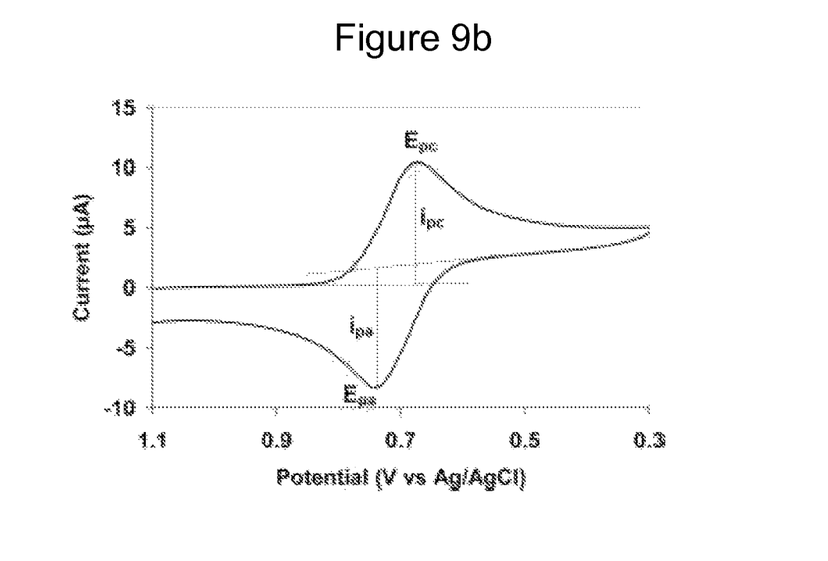
FIG. 9b shows an example of cyclic voltammetry measurements.

As shown in FIG. 9a, the applied voltage is ramped up and down in a controlled cyclic manner and the resulting current is measured at the first electrode. FIG. 9b shows an example of a typical I/V curve obtained using this method. The current peaks occur where the applied voltage matches the electrochemical potential (activation energy) of a particular reduction ($E_{pc}$) or oxidation ($E_{pa}$) reaction. The positioning of the peaks can therefore be used to study the chemical reactions and identify the analyte(s). In some cases, the electrical conductance of the first electrode can influence the height of the current peaks which may also be used to determine the presence and/or amount of analyte.

Figure 10:
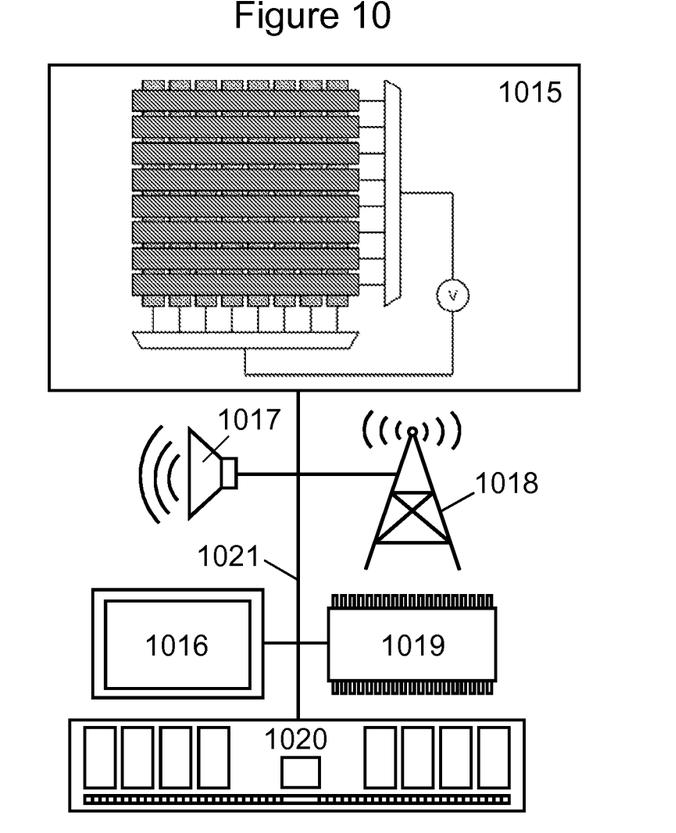
FIG. 10 shows an apparatus according to another embodiment of the present disclosure.

FIG. 10 shows another example of the present apparatus (comprising the plurality of first electrodes, the plurality of second electrodes, the electrolyte, the terminals and the measurement circuit shown in dashed box 505) further comprising an electronic display 1016, a loudspeaker 1017, a transmitter 1018 (or transceiver), a processor 1019 and a storage medium 1020 as part of the measurement circuit, which are electrically connected to one another by a data bus 1021. The apparatus may be one or more of an electronic device, a portable electronic device, a portable telecommunications device, a sensor array, and a module for any of the aforementioned devices.

In some embodiments, the measurement circuit may be configured to measure the electrical property of the sensor nodes and present the raw data to a user of the apparatus so that he/she can manually detect the presence of the analyte and quantify it based on this measurement. In other embodiments, however, the measurement circuit may be configured to determine the presence and/or amount of analyte automatically using the electrical property measurement and indicate the result to the user (with or without an indication of the electrical property measurement). This feature therefore provides the user with the end result without requiring him/her to derive it from the raw data.

The electronic display 1016 and loudspeaker 1017 are configured to present the electrical property measurements from the sensor nodes (and/or an indication of the presence and/or quantity of analyte) to a user of the apparatus, whilst the transmitter/transceiver 1018 is configured to transmit the data to another device. The transmitter/transceiver 1018 therefore enables the user to monitor the presence and/or quantity of analyte from a remote location.

The processor 1019 is configured for general operation of the apparatus by providing signalling to, and receiving signalling from, the other components to manage their operation. The storage medium 1020 is configured to store computer code configured to perform, control or enable operation of the apparatus. The storage medium 1020 may also be configured to store settings for the other components. The processor 1019 may access the storage medium 1020 to retrieve the component settings in order to manage the operation of the other components. The processor 1019 may be a microprocessor, including an Application Specific Integrated Circuit (ASIC). The storage medium 1020 may be a temporary storage medium such as a volatile random access memory. On the other hand, the storage medium 1020 may be a permanent storage medium such as a hard disk drive, a flash memory, or a non-volatile random access memory.

In embodiments where the measurement circuit is configured to automatically determine whether, and how much of, the analyte is present, the processor 1019 may also be configured to receive the electrical property measurement and compare this with predetermined calibration data (e.g. predetermined measurements of potential difference versus analyte concentration) from the storage medium 1020.

Figure 11A:
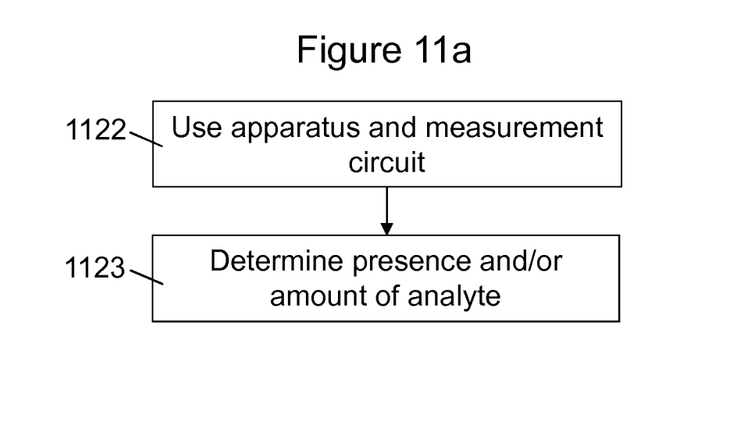
FIG. 11a shows the main steps of a method of determining the presence and/or amount of analyte using the apparatus described herein.

The main steps 1122-1123 of a method of using the apparatus in determining the presence and/or amount of analyte are shown schematically in FIG. 11*a*. Similarly, the main steps 1124-1125 of a method of making the apparatus are shown schematically in FIG. 11*b*.

A number of different fabrication processes may be used to form the present apparatus. In particular, the whole device may be made using screen printing, gravure printing, ink-jet printing or roll-to-roll printing, thereby lowering its manufacturing cost significantly. In this scenario, any components of the associated measurement circuit which cannot be directly printed may be bonded to the apparatus using a conductive epoxy.

Figure 12:
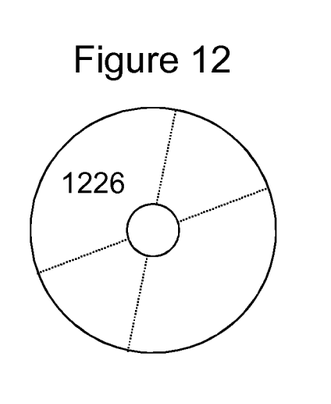
FIG. 12 shows a computer-readable medium comprising a computer program configured to perform, control or enable one or more of the method steps of FIG. 11a or 11b.

FIG. 12 illustrates schematically a computer/processor readable medium 1226 providing a computer program according to one embodiment. In this example, the computer/processor readable medium 1226 is a disc such as a digital versatile disc (DVD) or a compact disc (CD). In other embodiments, the computer/processor readable medium 1226 may be any medium that has been programmed in such a way as to carry out an inventive function. The computer/processor readable medium 1226 may be a removable memory device such as a memory stick or memory card (SD, mini SD, micro SD or nano SD).

Figure 11B:
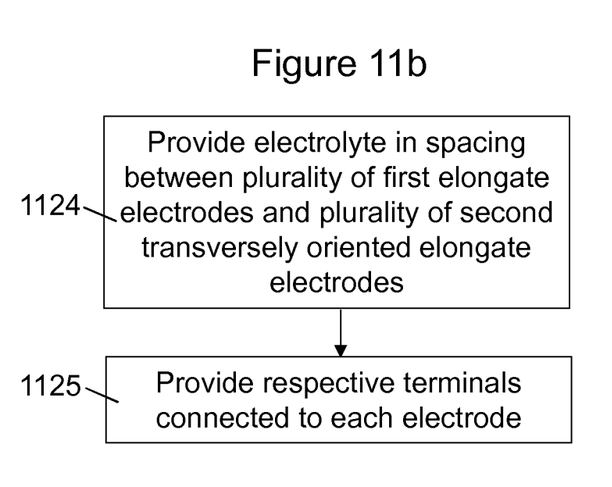
FIG. 11b shows the main steps of a method of making the apparatus described herein.

The computer program may comprise computer code configured to perform, control or enable one or more of the method steps 1122-1123, 1124-1125 of FIG. 11*a* or 11*b*. In particular, the computer program may be configured to measure the electrical property of the sensor nodes, and may also be configured to determine the presence and/or amount of analyte based on the electrical property measurement. Additionally or alternatively, the computer program may be configured to control the above-mentioned fabrication processes to form/assemble the apparatus.

Other embodiments depicted in the figures have been provided with reference numerals that correspond to similar features of earlier described embodiments. For example, feature number 1 can also correspond to numbers 101, 201, 301 etc. These numbered features may appear in the figures but may not have been directly referred to within the description of these particular embodiments. These have still been provided in the figures to aid understanding of the further embodiments, particularly in relation to the features of similar earlier described embodiments.

It will be appreciated to the skilled reader that any mentioned apparatus/device and/or other features of particular mentioned apparatus/device may be provided by apparatus arranged such that they become configured to carry out the desired operations only when enabled, e.g. switched on, or the like. In such cases, they may not necessarily have the appropriate software loaded into the active memory in the non-enabled (e.g. switched off state) and only load the appropriate software in the enabled (e.g. on state). The apparatus may comprise hardware circuitry and/or firmware. The apparatus may comprise software loaded onto memory. Such software/computer programs may be recorded on the same memory/processor/functional units and/or on one or more memories/processors/functional units.

In some embodiments, a particular mentioned apparatus/device may be pre-programmed with the appropriate software to carry out desired operations, and wherein the appropriate software can be enabled for use by a user downloading a "key", for example, to unlock/enable the software and its associated functionality. Advantages associated with such embodiments can include a reduced requirement to download data when further functionality is required for a device, and this can be useful in examples where a device is perceived to have sufficient capacity to store such pre-programmed software for functionality that may not be enabled by a user.

It will be appreciated that any mentioned apparatus/circuitry/elements/processor may have other functions in addition to the mentioned functions, and that these functions may be performed by the same apparatus/circuitry/elements/processor. One or more disclosed aspects may encompass the electronic distribution of associated computer programs and computer programs (which may be source/transport encoded) recorded on an appropriate carrier (e.g. memory, signal).

It will be appreciated that any "computer" described herein can comprise a collection of one or more individual processors/processing elements that may or may not be located on the same circuit board, or the same region/ position of a circuit board or even the same device. In some embodiments one or more of any mentioned processors may be distributed over a plurality of devices. The same or different processor/processing elements may perform one or more functions described herein.

It will be appreciated that the term "signalling" may refer to one or more signals transmitted as a series of transmitted and/or received signals. The series of signals may comprise one, two, three, four or even more individual signal components or distinct signals to make up said signalling. Some or all of these individual signals may be transmitted/received simultaneously, in sequence, and/or such that they temporally overlap one another.

With reference to any discussion of any mentioned computer and/or processor and memory (e.g. including ROM, CD-ROM etc), these may comprise a computer processor, Application Specific Integrated Circuit (ASIC), field-programmable gate array (FPGA), and/or other hardware components that have been programmed in such a way to carry out the inventive function.

The applicant hereby discloses in isolation each individual feature described herein and any combination of two or more such features, to the extent that such features or combinations are capable of being carried out based on the present specification as a whole, in the light of the common general knowledge of a person skilled in the art, irrespective of whether such features or combinations of features solve any problems disclosed herein, and without limitation to the scope of the claims. The applicant indicates that the disclosed aspects/embodiments may consist of any such individual feature or combination of features. In view of the foregoing description it will be evident to a person skilled in the art that various modifications may be made within the scope of the disclosure.

While there have been shown and described and pointed out fundamental novel features as applied to different embodiments thereof, it will be understood that various omissions and substitutions and changes in the form and details of the devices and methods described may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment may be incorporated in any other disclosed or described or suggested form or embodiment as a general matter of design choice. Furthermore, in the claims means-plus-function clauses are intended to cover the structures described herein as performing the recited function and not only structural equivalents, but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

The invention claimed is:

1. An apparatus comprising a plurality of first elongate electrodes separated from and electrically coupled to a plurality of second transversely oriented elongate electrodes by an electrolyte, the plurality of transversely oriented first and second electrodes forming an array of respective electrochemical sensor nodes at the spaced crossings thereof,
   wherein the first electrodes are configured such that the interaction of an analyte from a surrounding environment with the first electrode at a sensor node affects an electrical property of the sensor node, and
   wherein the apparatus comprises respective terminals connected to each electrode for electrical connection to a measurement circuit to enable determination of the presence and/or amount of analyte at a particular sensor node based on a measurement of the electrical property of that sensor node.

2. The apparatus of claim 1, wherein the first and second electrodes are configured to exhibit a potential difference therebetween, or a change in potential difference therebetween, on interaction of the first electrode with the analyte, the first electrodes configured such that one or more of their electrochemical potential and electrical conductance are dependent upon the amount of analyte present.

3. The apparatus of claim 2, wherein the measurement circuit forms part of the apparatus, the measurement circuit configured to measure the potential difference at the sensor nodes to enable determination of the presence and/or amount of analyte.

4. The apparatus of claim 1, wherein the apparatus is configured such that the first and second electrodes at a sensor node serve as the anode and cathode of an electrochemical sensor, and the second electrode serves as a reference electrode with respect to which the potential of the first electrode is measured.

5. The apparatus of claim 1, wherein the apparatus comprises a further electrode separated from the plurality of second electrodes by an electrolyte, and wherein the apparatus is configured such that the first and further electrode at a sensor node serve as the anode and cathode of an electrochemical sensor, and the second electrode serves as a reference electrode with respect to which the potential of the first electrode is measured.

6. The apparatus of claim 5, wherein the apparatus comprises a feedback loop between the second electrode and the further electrode to hold the second electrode at a reference potential.

7. The apparatus of claim 1, wherein the measurement circuit forms part of the apparatus, the measurement circuit configured to apply a varying potential difference between the first and second electrode at a sensor node and measure current peaks at the first electrode in response to the applied potential difference, and wherein the first electrode is configured such that the position and/or size of the current peaks are dependent upon the presence and/or amount of analyte.

8. The apparatus of claim 1, wherein the plurality of first electrodes are configured such that the electrical property of each sensor node is dependent upon the presence and/or amount of the same analyte.

9. The apparatus of claim 8, wherein the first electrode at each sensor node comprises the same material.

10. The apparatus of claim 1, wherein at least some of the plurality of first electrodes are configured such that the electrical property of the respective sensor nodes is dependent upon the presence and/or amount of different analytes.

11. The apparatus of claim 10, wherein the first electrodes at the respective sensor nodes comprise different materials or the same material with different functionalizations to allow the presence and/or amount of the different respective analytes to be determined.

12. The apparatus of claim 1, wherein the measurement circuit forms part of the apparatus, the measurement circuit comprising a first multiplexer connected to the terminals of the plurality of first electrodes and a second multiplexer connected to the terminals of the plurality of second electrodes, the first and second multiplexers configured to enable the electrical property of a particular sensor node to be selectively determined.

13. The apparatus of claim 1, wherein the apparatus is configured such that the plurality of first electrodes are arranged substantially parallel to one another, the plurality of second electrodes are arranged substantially parallel to one another, and the plurality of first electrodes are arranged substantially perpendicular to the plurality of second electrodes.

14. The apparatus of claim 1, wherein the apparatus comprises microfluidic channels and associated pumps configured to deliver fluid to the sensor nodes for determination of the presence and/or amount of analyte within the fluid.

15. The apparatus of claim 1, wherein one or more of the first electrodes comprise a graphene oxide film.

16. The apparatus of claim 1, wherein the analyte comprises water.

17. The apparatus of claim 1, wherein the apparatus is one or more of an electronic device, a portable electronic device, a portable telecommunications device, a sensor array, and a module for any of the aforementioned devices.

18. A method comprising determining the presence and/or amount of analyte using an apparatus and a measurement circuit, the method comprising:

providing the apparatus comprising a plurality of first elongate electrodes separated from and electrically coupled to a plurality of second transversely oriented elongate electrodes by an electrolyte, the plurality of transversely oriented first and second electrodes forming an array of respective electrochemical sensor nodes at the spaced crossings thereof, configuring the first electrodes such that the interaction of an analyte from a surrounding environment with the first electrode at a sensor node affects an electrical property of the sensor node, connecting respective terminals of the apparatus to each electrode for electrical connection to a measurement circuit; and determining the presence and/or amount of analyte at a particular sensor node based on a measurement of the electrical property of that sensor node.

19. A method of making an apparatus for use in determining the presence and/or amount of analyte, the method comprising:

providing an electrolyte in a spacing between and electrically coupling a plurality of first elongate electrodes and a plurality of second transversely oriented elongate electrodes to form an array of respective electrochemical sensor nodes at spaced crossings of the first and second electrodes, wherein the first electrodes are configured such that the interaction of an analyte from a surrounding environment with the first electrode at a sensor node affects an electrical property of the sensor node; and providing respective terminals connected to each electrode for electrical connection to a measurement circuit to enable determination of the presence and/or amount of analyte at a particular sensor node based on a measurement of the electrical property of that sensor node.

* * * * *